US007332331B2

(12) United States Patent
Yashiro

(10) Patent No.: US 7,332,331 B2
(45) Date of Patent: Feb. 19, 2008

(54) **PLASMID SHUTTLE VECTOR BETWEEN *ESCHERICHIA COLI* AND *BREVIBACILLUS***

(75) Inventor: Koji Yashiro, Chiba (JP)

(73) Assignee: Higeta Shoyu Co., Ltd., Tokyo (JP)

( * ) Notice: Subject to any disclaimer, the term of this patent is extended or adjusted under 35 U.S.C. 154(b) by 515 days.

(21) Appl. No.: 10/467,930

(22) PCT Filed: Feb. 7, 2002

(86) PCT No.: PCT/JP02/01038

§ 371 (c)(1),
(2), (4) Date: Aug. 14, 2003

(87) PCT Pub. No.: WO02/064800

PCT Pub. Date: Aug. 22, 2002

(65) Prior Publication Data

US 2004/0072328 A1 Apr. 15, 2004

(30) Foreign Application Priority Data

Feb. 14, 2001 (JP) ............................ 2001-037167

(51) Int. Cl.
*C07H 21/04* (2006.01)
*C12N 1/20* (2006.01)
*C12N 15/00* (2006.01)
*C12P 21/06* (2006.01)

(52) U.S. Cl. .............................. 435/320.1; 435/252.3; 536/23.1

(58) Field of Classification Search ............... 435/69.1, 435/252.3, 320.1; 536/23.1
See application file for complete search history.

(56) References Cited

FOREIGN PATENT DOCUMENTS

| | | |
|---|---|---|
| GB | 2182664 A * | 5/1987 |
| JP | 62-83890 | 4/1987 |
| JP | 62-201583 | 9/1987 |
| JP | 63-198986 | 8/1988 |
| JP | 1-58950 | 12/1989 |
| JP | 2-135091 | 5/1990 |
| JP | 4-278091 | 10/1992 |
| JP | 7-170984 | 7/1995 |
| JP | 9/224677 | 9/1997 |
| JP | 2727391 | 12/1997 |
| JP | 2787585 | 6/1998 |
| JP | 10-295378 | 11/1998 |
| JP | 2000-197491 | 7/2000 |

OTHER PUBLICATIONS

H. Yamagata et al. J. Bacteriol., vol. 169, pp. 1239-1245 1987.
Shigezo Udada Nippon Nogeikagaku Kaishi, vol. 61, pp. 669-676 1987.
M. Takano et al. Appln. Microbiol. Biotechnol., vol. 30, pp. 75-80 1989.
H. Yamagata et al. Proc. Natl. Acad. Sci., USA, vol. 86, pp. 3589-3593, 1989.
Y. Shiga et al. Applied and Environmental Microbiology, vol. 58, pp. 525-531, 1992.
T. Ishihara et al. J. Bacteriol., vol. 177, pp. 745-749, 1995.
T. Takagi et al. Agric. Biol. Chem., vol. 53, pp. 3099-3100, 1989.
O. Shida et al. Int. J. Syst. Bacteriol., vol. 46, pp. 939-946, 1996.
Clements and Finkelstein Intect. Immun., vol. 24, pp. 760-769, 1979.
G. Del Solar et al. Mol. Microbiol., vol. 8, pp. 789-796, 1997.
K. Sano et al. FEMS Microbiology Letters, vol. 148, pp. 223-226, 1997.
T. Kajino et al. Appln. Environ. Microbiol., vol. 66, pp. 638-642, 2000.
S. Udaka et al. Methods in Enzymology, vol. 217, pp. 23-33, 1993.
N. Saito Arch. Biochem. Biophys., vol. 155, pp. 290-298, 1973.
J. Mekalanos et al Nature, vol. 306, pp. 551-557, 1983.
Yashiro K. Et al., High-level production of recombinant chicken interferon-gamma by *Brevibacillus choshinensis*. Protein Expression and Purification, Oct. 2001, 23(1) p. 113-20.
Le Grice S.F. et al,. Expression of biologically active human T-cell lymphotropic virus type III reverse transcriptase in *Bacillus subtilis*. Gene, 1987, 55(1), pp. 95-103.
Yoshiyuki Sakaki, Vector DNA, Kodansha Scientific, Aug. 10, 1991, Pates 93 to 95.
Sun L. et al., Transfer of shuttle vectors containing *Bacillus thuringiensis* toxin gene into wild-type *B. cereus*, *B. brevis* and *B. subtilis* by electroporation. Chinese Journal of Biotechnology, 1994, 10(1), pp. 1-9.
Shiroza T, et al,. Construction of a chimeric shuttle plasmid via a heterodimer system: secretion of an scFv protein from *Bacillus brevis* cells capable of inhibiting hemagglutination. Biosci Biotechnol Biochem, Feb. 2001, 65(2), p. 389-95.
Shogo Ebisu, et al., "Conserved Structures of Cell Wall Protein Genes among Protein-Producing *Bacillus brevis* Strains", Journal of Bacteriology, vol. 172, No. 3, XP-000940881, Mar. 1990, pp. 1312-1320.
Takahiro Adachi, et al., "Multiple and Tandemly Arranged Promoters of the Cell Wall Protein Gene Operon in *Bacillus brevis* 47",Journal of Bacteriology, American Society for Microbiology, vol. 171, No. 2, Feb. 1989, pp. 1010-1016.

* cited by examiner

*Primary Examiner*—Mark Navarro
(74) *Attorney, Agent, or Firm*—Oblon, Spivak, McClelland, Maier & Neustadt, P.C.

(57) ABSTRACT

The invention provides a plasmid shuttle vector characterized by being replicable in both of bacteria of the genus *Brevibacillus* and *Escherichia coli*, and by comprising a promoter capable of functioning in bacteria of the genus *Brevibacillus* and a DNA sequence(s) capable of functioning as a selective marker(s) for *Escherichia coli* and bacteria of the genus *Brevibacillus*, and a method of transforming bacteria of the genus *Brevibacillus* using the said plasmid shuttle vector. The plasmid shuttle vector enables the efficient transformation of bacteria of the genus *Brevibacillus*. Further, since plasmid shuttle vector pNCMO2 of the invention in particular has a gene expression control region which efficiently expresses and secretes an objective gene in bacteria of the genus *Brevibacillus* but significantly suppresses the expression in *Escherichia coli*, a recombinant gene expression plasmid can efficiently be constructed using *Escherichia coli*, and it is suited for protein production in bacteria of the genus *Brevibacillus*.

8 Claims, 10 Drawing Sheets

Fig. 1 aaggcgccgc aacttttgat tcgctcaggc gtttaatagg atgt 44

Fig. 2 aattgtgagc ggataacaat t 21

Fig. 3 gaaaggaggt 10

Fig. 4 agaggaggag aa 12

Fig. 5 atg aaa aaa aga agg gtc gtt aac agt gta ttg ctt ctg cta ctg cta gct agt gca ctc 60
Met Lys Lys Arg Arg Val Val Asn Ser Val Leu Leu Leu Leu Leu Leu Ala Ser Ala Leu gca ctt act gtt gct ccc atg gct ttc gct 90
Ala Leu Thr Val Ala Pro Met Ala Phe Ala

Fig. 6 aaaatgcatg gccagcaaaa gg 22

Fig. 7 aaaatgcatg acgaaagggc 20

Fig. 8 aaatgatcaa agcttcggca ttatagtgcg gg 32

Fig. 9 aaatgatcct gcaggatccg tcgactctag

Fig. 10 aaaggatccg acataatgga cagg 24

Fig. 11 aaactgcaga ataattgtta tccgctcaca attacatcct attaaacgcc tg 52

Fig. 12 aaactgcatg gctttcctgc gaaagg 26

Fig. 13 aaaagcttat cgatttcgaa ggg 23

Fig. 14 cgctgcagca gcggcggcaa atc 23

Fig. 15 aaaagcttat ctttgaacat aaattg 26

Fig. 16 aaccatggct ttcgctaatg atgataagtt atat 34

Fig. 17 ttaagcttca taattcatcc ttaattct 28

Fig. 18 aaccatggct ttcgctacac ctcaaaatat tactgatttg tgtgcagaat accacaac 58

Fig. 19 aaggatcctt aatttgccat actaattgcg gc 32

Fig. 20 gcggatccag aggaggagaa cacaaggtc 29

P2 : P2 Promoter
P5 : P5 Promoter
Op : *lac* operator sequence
SP : HWP signal sequence
MCS : multicloning site
Amp$^r$ : ampicillin resistance gene
Nm$^r$ : neomycin resistance gene
Rep : Rep protein gene from pUB110
-Ori : pUB110 -Ori
Ori : ColE1 Ori P2 : P2 Promoter
P5 : P5 Promoter
Op : lac operator sequence
SP : HWP signal sequence
SP' : R2L6 type modified HWP signal sequence
SD : SD sequence
MCS : multicloning site
$Amp^r$ : ampicillin resistance gene
$Nm^r$ : neomycin resistance gene
Rep : Rep protein gene from pUB110
-Ori : pUB110 -Ori
Ori : ColE1 Ori BLA : α- amylase from *Bacillus licheniformis*

$Em^r$ : erythromycin resistance gene

P2 : P2 Promoter

P5 : P5 Promoter

SP : HWP signal sequence

SP' : R2L6 type modified HWP signal sequence

SD : SD sequence

MCS : multicloning site $Amp^r$ : ampicillin resistance gene $Nm^r$ : neomycin resistance gene Rep :Rep protein gene from pUB110

-Ori : pUB110 - Ori

Ori : ColE1 Ori

BLA : α - amylase from *Bacillus licheniformis*

$Em^r$ : erythromycin resistance gene

P2 : P2 Promoter

P5 : P5 Promoter

Op : *lac* operator sequence

SP' : R2L6 type modified HWP signal sequence

SD : SD sequence

MCS : multicloning site $Amp^r$ : ampicillin resistance gene $Nm^r$ : neomycin resistance gene Rep :rep protein gene from pUB110

- Ori : pUB110 - Ori

Ori : ColE1 Ori

SDS-PAGE sample 4 μl/lane

CBB stain

Western blotting using anti-CT antibody

M: marker

S: pNCMO2 CT/*B. choshinensis* HPD31- S5 culture supernatant

PLASMID SHUTTLE VECTOR BETWEEN *ESCHERICHIA COLI* AND *BREVIBACILLUS*

TECHNICAL FIELD TO WHICH THE INVENTION BELONGS

The present invention relates to a plasmid shuttle vector between *Escherichia coli* and bacteria of the genus *Brevibacillus* and a method of transforming bacteria of the genus *Brevibacillus* using the plasmid shuttle vector. More specifically, it relates to a plasmid shuttle vector which has a gene expression control region effectively expressing and secreting an objective gene product in bacteria of the genus *Brevibacillus* but significantly suppressing the expression in *Escherichia coli*, and which is suited for gene expression in bacteria of the genus *Brevibacillus*. Further, it relates to a process for producing a protein, characterized by culturing a transformant transformed by the transformation method.

PRIOR ART

Udaka et al. have succeeded in the development of an expression system of a recombinant protein using as a host bacteria of the genus *Brevibacillus* (separated from the ordinary classification of the genus *Bacillus*) having excellent characteristics, not found in *Escherichia coli* and *Bacillus subtilis*, that a large amount of a protein is secreted extracellularly and an extracellular protease activity is weak (Japan Patent No. 2082727, JP-A 62-201583 (1987), Yamagata, H. et al., J. Bacteriol., 169, 1239-1245 (1987), Shigezo Udaka, Nippon Nogeikagaku Kaishi 61, 669-676 (1987), Takao, M. et al., Appl. Microbiol, Blotechnol., 30, 75-80 (1989), Yamagata, H. et al., Proc. Natl. Acad. Sci., USA 86, 3589-3593 (1989)). Production of α-amylase (Japanese Patent No. 2082727) or human epidermal growth factor (hEGF) (Japanese Patent No. 2787585) by an expression system using bacteria of the genus Brevibacillus as a host, and the like have been so far reported.

Meanwhile, as a plasmid vector useful for gene expression of bacteria of the genus Brevibacillus, for example, pNU200 (Shigezo Udaka, Nippon Nogeikagaku Kaishi 61, 669-676 (1987)), pNH300 (Shiga, Y. et al., Applied and Environmental Microbiology, 58, 525-531 (1992)), pNH400 (Ishihara, T, et al., J. Bacteriol., 177, 745-749 (1995)), pHY700 (JP-A 4-278091 (1992), pHT series plasmids (Japanese Patent No. 2727391) and the like have been so far reported. Especially, the present inventors applied pNY301 and other pNY series plasmids for patent (JP-A 10-295378) as a plasmid vector useful for transformation of bacteria of the genus *Brevibacillus.*

Problems that the Invention is to Solve

As mentioned above, the secretory production system of proteins using bacteria of the genus *Brevibacillus* as a host is one of useful systems in production of proteins by genetic recombination. However, a transformation efficiency of bacteria of the genus *Brevibacillus* is low in comparison to a transformation efficiency of *Escherichia coli*. Accordingly, there was a defect that construction of recombinant gene expression plasmids using bacteria of the genus *Brevibacillus* is difficult in comparison to *Escherichia coli*. For example, in case of using an electroporation method (Takagi, T. et al, Agric. Biol. Chem., 53, 3099-3100 (1989)), a transformation efficiency of *Escherichia coli* reaches $10^{10}$ CFU/ugDNA. Meanwhile, in case of *Brevibacillus choshinensis* (*Bacillus brevis* before; there was a change in taxonomical position in Shida O., et al., Int. J. Syst. Bacteriol., 46, 939-946 (1996)) belonging to the genus *Brevibacillus*, it was only $10^7$ CFU/ugDNA. Further, it has been known that in case of employing a method except the electroporation method, the transformation efficiency of bacteria of the genus *Brevibacillus* is more reduced.

Especially, transformation of bacteria of the genus *Brevibacillus* with a gene encoding a protein having a complex quaternary structure, for example, a gene encoding a protein such as cholera toxin (CT) produced from *Vibrio cholerae* comprising one A subunit and five B subunits (Clements and Finkelstein, Intect. Immun., 24; 760-769 (1979)) and protein production using the transformant have to date experienced a great many difficulties.

As one of measures to cope with the problems, a method is considered in which a plasmid vector (hereinafter referred to as a "shuttle vector") replicable also in other host cells easy of a transformation step, for example, *Escherichia coli* is used, construction of a recombinant gene expression plasmid using the host cells is first constructed and transformation of bacteria of the genus *Brevibacillus* is further conducted by electroporation or the like using the recombinant gene expression plasmid.

A shuttle vector and a transformation method using the shuttle vector are techniques known to those skilled in the art. For example, with respect to a shuttle vector between *Escherichia coli* and *Bacillus subtilis*, JP-A 63-198986 (1988), JP-A 2000-197491 and the like have been reported. Nevertheless, a plasmid shuttle vector utilizable in a transformation procedure by genetic recombination of bacteria of the genus *Brevibacillus* and in recombinant gene expression with the transformant, and a method of transforming bacteria of the genus *Brevibacillus* using the said plasmid shuttle vector have been to date unknown.

Means for Solving the Problems

The present inventors have focussed on such usefulness that an objective protein is extracellularly secreted in an expression system using bacteria of the genus *Brevibacillus* as a host, have seriously considered the necessity for the development of a novel host-vector system that solves the foregoing defects, and have tried to develop a novel plasmid shuttle vector in which *Escherichia coli* and bacteria of the genus *Brevibacillus* can be used as a host and which can be used in genetic recombination.

Thus, in order to attain the object, the present inventors have focussed again on the point that especially plasmid vector pNY301 which the present inventors have already applied for patent, among a large number of plasmid vectors, contains a promoter and a secretion signal sequence from *Brevibacillus choshinensis* HPD31. Based on this plasmid vector pNY301, they have synthesized various DNA sequences by PCR or the like, or cut them out from known sequences, further inserted these DNA fragments into the plasmid vector and confirmed the insertion. Moreover, they have performed confirmation of transformation with the resulting plasmids, confirmation of expression in transformants, and so forth. As a result of performing a huge number of these delicate treatments and operations with trial and error, they have finally succeeded in production of a desired novel plasmid shuttle vector.

The novel plasmid shuttle vector which has been successfully produced in this manner has been introduced into *Escherichia coli* and bacteria of the genus *Brevibacillus*, and the resulting bacteria have been cultured. Consequently, replication of the plasmid shuttle vector has been performed in any of the hosts. It has been found that in the recombinant gene product expression using the plasmid shuttle vector, an objective gene is effectively secreted and expressed in bacteria of the genus *Brevibacillus*, but the expression is significantly suppressed in *Escherichia coli*. It has been further confirmed that even though a transformant of bacteria of the genus *Brevibacillus* is not obtained by other known methods, the transformation is enabled with the use of the plasmid shuttle vector. Thus, the invention has been completed.

That is, for solving the foregoing problems, the invention provides a plasmid shuttle vector between *Escherichia coli* and bacteria of the genus *Brevibacillus* which is useful for transformation by genetic recombination of bacteria of the genus *Brevibacillus* and for protein production with the transformant, and a transformation method using the plasmid shuttle vector. Especially, it provides a plasmid shuttle vector having a gene expression control region which efficiently expresses and secretes an objective gene product in bacteria of the genus *Brevibacillus*, but which significantly suppresses the expression in *Escherichia coli*, and being suited for gene expression in bacteria of the genus *Brevibacillus* and for protein production. Further, the invention provides a method of transforming bacteria of the genus *Brevibacillus* using the plasmid shuttle vector, and a process for producing a protein, characterized by culturing bacteria of the genus *Brevibacillus* transformed with the plasmid shuttle vector.

BRIEF DESCRIPTION OF THE DRAWINGS

FIG. 1 shows a P2 promoter.

FIG. 2 shows a Lac operator sequence.

FIG. 3 shows an SD sequence (SD1).

FIG. 4 shows an SD sequence (SD2).

FIG. 5 shows an R2L6 type modified signal peptide (nucleotide sequence in upper column, and amino acid sequence in lower column).

FIG. 6 shows PCR cloning primer 1.

FIG. 7 shows PCR cloning primer 2.

FIG. 8 shows PCR cloning primer 3.

FIG. 9 shows PCR cloning primer 4.

FIG. 10 shows PCR cloning primer 5.

FIG. 11 shows PCR cloning primer 6.

FIG. 12 shows PCR cloning primer 7.

FIG. 13 shows PCR cloning primer 8.

FIG. 14 shows PCR cloning primer 9.

FIG. 15 shows PCR cloning primer 10.

FIG. 16 shows PCR cloning primer 11.

FIG. 17 shows PCR cloning primer 12.

FIG. 18 shows PCR cloning primer 13.

FIG. 19 shows PCR cloning primer 14.

FIG. 20 shows PCR cloning primer 15.

MODE FOR CARRYING OUT THE INVENTION

Figure 21:
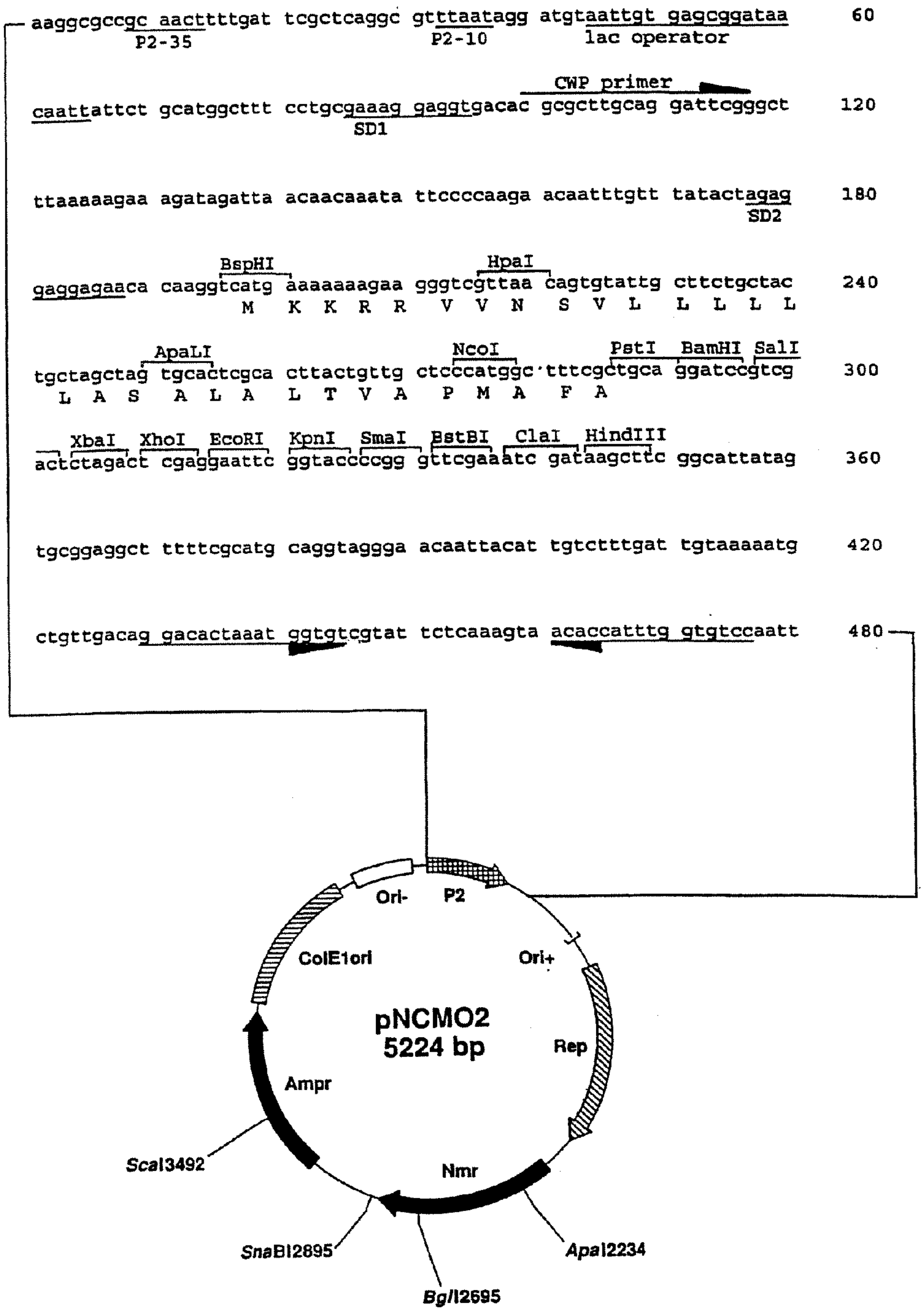
FIG. 21 shows a restriction map of plasmid shuttle vector pNCMO2.

The invention is described in detail below.

The plasmid shuttle vector of the invention is a plasmid shuttle vector replicable in both of *Escherichia coli* and bacteria of the genus *Brevibacillus*, and comprising a promoter capable of functioning in bacteria of the genus *Brevibacillus*, and a DNA sequence(s) encoding a selective marker(s) for bacteria of the genus *Brevibacillus* and *Escherichia coli*.

The plasmid shuttle vector of the invention is autonomously replicable in *Escherichia coli* and bacteria of the genus *Brevibacillus*. Accordingly, a recombinant gene expression plasmid can be constructed by a step such as insertion of a DNA fragment in the plasmid shuttle vector of the invention using *Escherichia coli*, and further transformation of bacteria of the genus *Brevibacillus* can be performed using the recombinant gene expression plasmid.

The promoter capable of functioning in bacteria of the genus *Brevibacillus*, which the plasmid shuttle vector of the invention possesses, is not particularly limited so long as it functions in bacteria of the genus *Brevibacillus*. It is preferably a promoter from bacteria of the genus *Brevibacillus*. Especially preferable examples thereof can include promoters contained in an MWP promoter region from *Brevibacillus brevis* 47 (*Bacillus brevis* 47 before)(JP-B 1-58950 (1989) and JP-B 7-108224 (1995)) and an HWP promoter region from *Brevibacillus choshinensis* HPD31 (FERM BP-6863)(*Bacillus brevis* before; this strain is the same as *Bacillus brevis* H102 (FERM BP-1087)(JP-A4-278091 (1992) and JP-A6-133782 (1994)), for example, a P2 promoter (Sequence No. 1: FIG. 1).

The plasmid shuttle vector of the invention further comprises a ribosome-binding region (SD sequence) and a DNA sequence encoding a signal peptide for secreting an expression protein (secretion signal sequence) at the 3'-terminus of a promoter functioning in bacteria of the genus *Brevibacillus*. As the SD sequence, for example, a sequence from an HWP gene expression control region of *Brevibacillus choshinensis*, such as SD1 (Sequence No. 3: FIG. 3) or SD2 (sequence No. 4: FIG. 4) can be used. As the secretion signal sequence, for example, a signal sequence contained in an HWP promoter region of *Brevibacillus choshinensis* HPD31 (FERM BP-1087, FERM BP-6863) can be used. As an especially preferable example, a modified HWP signal sequence of R2L6 type or the like (JP-A 7-170984 (1995)) can be mentioned (with respect to this R2L6 type modified signal sequence, its amino acid sequence is shown in Sequence No. 5, and its DNA sequence is shown in Sequence No. 21. Further, both of the sequences are shown in FIG. 5. In the drawing, the upper column shows a nucleotide sequence, and the lower column shows an amino acid sequence).

The plasmid shuttle vector of the invention further comprises the DNA sequence encoding a replication control region necessary for replication in bacteria. With respect to the replication control region, either one common region or different regions may be used for both of bacteria of the genus *Brevibacillus* and *Escherichia coli*. The replication control region in bacteria of the genus *Brevibacillus* comprises a Rep protein gene and an origin of replication. The sequence capable of functioning as a replication control region in bacteria of the genus *Brevibacillus* is not particularly limited so long as it is contained in a plasmid which is replicated and grown in bacteria of the genus *Brevibacillus* and is a DNA sequence functioning as a replication control region of a plasmid. As an especially preferable example, a Rep protein gene from plasmid pUB110 and a DNA sequence encoding an origin of replication can be mentioned.

In *Escherichia coli*, an origin of replication is required as a replication control region. A DNA sequence encoding an origin of replication capable of functioning in *Escherichia coli* is not particularly limited so long as it is a DNA sequence contained in a plasmid replicated and grown in *Escherichia coli* and functioning as an origin of replication of a plasmid. Preferable is a DNA sequence containing an ori region functioning as an origin of replication of a plasmid. Especially preferable is a DNA sequence encoding an ori region of plasmid vectors ordinarily used in a genetic recombination manipulation using *Escherichia coli*, such as pUC series, for example, pUC18, pUC118 and pUC119, and pBR322.

As a DNA sequence encoding a replication control region capable of functioning in both of bacteria of the genus *Brevibacillus* and *Escherichia coli*, a replication control region of a plasmid belonging to a pLS1/pE194 plasmid family, which is a replication control region capable of functioning in both of Gram-positive bacteria and Gram-negative bacteria (Del Solar, G. et al., Mol. Microbiol., 8, 789-796 (1993)) can be mentioned. For example, a DNA sequence encoding a replication control region (Sano. K. et al., FEMS Microbiology Letters, 148, 223-226 (1997)) comprising ori, RepA and RepB of plasmid pLA106 from *Lactobacillus acidophilus* can be used.

With respect to sequences capable of functioning as selective markers for bacteria of the genus *Brevibacillus* and *Escherichia coli*, which the plasmid shuttle vector of the invention possesses, one common DNA sequence or different DNA sequences may be used to both of bacteria of the genus *Brevibacillus* and *Escherichia coli*. With respect to the sequences capable of functioning as the selective markers, a drug resistance gene can be used. For bacteria of the genus *Brevibacillus*, for example, a DNA sequence containing a drug resistance gene from bacteria of the genus *Brevibacillus* and bacteria of the genus *Bacillus analogous* thereto can be used. Especially preferable examples thereof can include a neomycin resistance gene contained in plasmid vector pNY301(JP-A 10-295378 (1998)) and an erythromycin resistance gene contained in pHT110 (Japanese Patent No. 2727391). Further, for *Escherichia coli*, for example, a DNA sequence encoding a kanamycin resistance gene, an ampicillin resistance gene, a chloramphenicol resistance gene or the like which is a known drug resistance gene from *Escherichia coli* is available. Still further, as a drug resistance gene capable of functioning in both of bacteria of the genus *Brevibacillus* and *Escherichia coli*, a zeocin resistance gene or the like can be used.

The plasmid shuttle vector of the invention can further comprise a DNA sequence having a function to suppress expression of recombinant gene in *Escherichia coli*. For example, in case of *Escherichia coli* having a lacI gene, a lac operator sequence (Sequence No. 2: FIG. 2) from *Escherichia coli* can be contained in the 3'-terminus of a promoter sequence functioning in bacteria of the genus *Brevibacillus*.

The plasmid shuttle vector of the invention is novel. For example, pNCMO2 is a plasmid vector having a size of 5,224 bp. A restriction map of pNCMO2 and a nucleotide sequence of its part containing a promoter were shown in FIG. 21. The promoter region of pNCMO2 contains a P2 promoter from an HWP promotor region of *Brevibacillus choshinensis* HPD31, a lac operator from *Escherichia coli*, an SD sequence, an R2L6 type modified signal sequence as a secretion signal sequence, a multicloning site and an HS gene (JP-A 9-224677 (1997)) as a terminator. With respect to the multicloning site, PstI, BamHI, SalI, XbaI, XhoI, EcoRI, KpnI, SmaI, ClaI, HindIII sites are available as cloning sites.

Plasmid shuttle vector pNCMO2 contains a DNA sequence encoding a neomycin resistance gene as a selective marker gene for bacteria of the genus *Brevibacillus*, a Rep protein gene from pUB110 necessary for replication in bacteria of the genus *Brevibacillus*, a ColE1 ori region as an origin of replication of *Escherichia coli* and an ampicillin resistance gene as a selective marker gene for *Escherichia coli*.

In the construction of plasmid shuttle vector pNCMO2 in the invention, pNY301, pNH326, pNU201 and the like are used. Plasmid pNY301 is laid open in JP-A 10-295378 (1998), plasmid pNH326 in Kajino., T., et al., Appl. Environ. Microbiol., 66, 638-642 (2000), and pNU201 in Udaka, S. et al., Methods in Enzymology, 217, 23-33 (1993) respectively, and these are known plasmids. Other plasmids which are used in construction of the plasmid shuttle vector of the invention can be procured on the market.

*Brevibacillus choshinensis* HPD31-S5/pNCMO2 carrying plasmid vector pNCMO2 was internationally deposited on Dec. 12, 2000 in Patent Microorganism Depository of National Institute of Bioscience and Human-Technology, Agency of Industrial Science and Technology, Ministry of International Trade and Industry (the present name: International Patent Organism Depositary, National Institute of Advanced Industrial Science and Technology, AIST Tsukuba Central 6,1-1, Higashi 1-chome, Tsukuba-shi, Ibaraki-ken, 305-8566, Japan), and it is assigned Receipt No. FERM BP-7394.

The host used in construction of the expression plasmid of the invention is not particularly limited so long as it is a strain belonging to *Escherichia coli*. As an especially preferable example, *E. coli* JM109 can be mentioned. *E. coli* JM109 is a known strain which can be procured on the market.

With respect to a method of constructing a recombinant gene expression plasmid from the plasmid shuttle vector of the invention using *Escherichia coli*, a method based on a standard technology of molecular biology known to a skilled person can be used properly. For example, the method described in Molecular Cloning 2nd ed., A Laboratory Manual, Cold Spring Harbor Laboratory (1989)) is mentioned. The details are described in Examples.

As the host used in the expression of the recombinant gene in the invention, any strain of bacteria of the genus *Brevibacillus* can be used. Preferable is *Brevibacillus choshinensis*. Especially preferable examples can include *Brevibacillus choshinensis* HPD31 (FERM BP-1087, FERM BP-6863), and *Brevibacillus choshinensis* HPD31-S5 (FERM BP-6623) which is a variant thereof.

As a method of transforming bacteria of the genus *Brevibacillus* using the shuttle vector of the invention and a recombinant gene expression plasmid constructed with *Escherichia coli*, a known transformation method known to a skilled person, such as electroporation, can be used.

A medium used in culture of the transformant of the invention contains, as required, a carbon source, a nitrogen source and inorganic salts. Culture may be conducted using a synthetic medium made mainly of saccharide and inorganic salts. In case of using a strain exhibiting auxotrophy, it is advisable to add nutrients required for its growth to a medium. Further, antibiotic, antifoam and the like may be added as required.

With respect to culture conditions, the initial pH of a medium is controlled to from 5.0 to 9.0, preferably from 6.5 to 7.5. The culture temperature is usually from 15° C. to 42° C., preferably from 24 to 37° C., and the culture time is usually from 16 to 360 hours, preferably from 24 to 144 hours. Bacteria of the genus *Brevibacillus* transformed by the method of the invention thereby produce and accumulate proteins in a culture solution.

After completion of the culture, collection of an objective protein from the culture is enabled by an appropriate combination of protein purification methods known to a skilled person, such as solvent extraction, ultrafiltration, ammonium sulfate fractionation, HPLC, gel filtration chromatography, ion exchange chromatography, affinity chromatography, hydrophobic interaction chromatography, electrophoresis and isoelectric focussing.

EXAMPLES

The invention is illustrated more specifically below by referring to Examples. However, this is illustrative, and the invention is not limited thereto.

Example 1

Construction of Plasmid Shuttle Vector pNCMO2

(1) Construction of Plasmid Shuttle Vector pNC301

Amplification was conducted by PCR with plasmid vector pUC119 as a template using primer 1 (Sequence No. 6: FIG. 6) and primer 2 (Sequence No. 7: FIG. 7), and the resulting PCR product was cleaved with NsiI to obtain a DNA fragment of approximately 2 kbp containing a ColE1 ori region as an origin of replication of *Escherichia coli* and an ampicillin resistance gene.

PCR was conducted such that a PCR kit (made by Takara Shuzo Co., Ltd.) was used, 100 pmol of each primer, 2.5 units of a Taq polymerase, 200 μM dNTP, 1 ng pUC119 template DNA and 100 μl Taq buffer (10 mM Tris-hydrochloride (pH 8.5), 2.5 mM $Mg^{++}$, 50 mM potassium chloride and 100 μg/ml bovine serum albumin) were mixed, the mixture was maintained at 96° C. for 30 seconds, and a cycle of DNA thermal denaturation (94° C., 60 sec), primer annealing (54° C., 60 sec) and primer elongation (70° C., 60 sec) was then repeated 25 times. This condition is hereinafter referred to as condition 1.

The above-obtained DNA fragment of approximately 2 kbp was ligated to an Sse8387I site of plasmid vector pNY301 (JP-A 10-295376 (1998)) containing a P5 promoter from an HWP promoter region of *Brevibacillus choshinensis* HPD3 1 and a natural type HWP signal sequence as a secretion signal sequence with a T4 DNA ligase using a DNA ligation kit (made by Takara Shuzo Co., Ltd.). *E. coli* JM109 (made by Takara Shuzo Co., Ltd.) was transformed with this DNA by the CaCl2 method (Molecular Cloning 2nd ed., A Laboratory Manual, Cold Spring Harbor Laboratory, 1, 82, (1989)), and a plasmid was extracted from the resulting ampicillin resistance transformant. The resulting plasmid was a novel plasmid shuttle vector replicable in *Escherichia coli* and bacteria of the genus *Brevibacillus*, and was designated pNC301.

Figure 22:
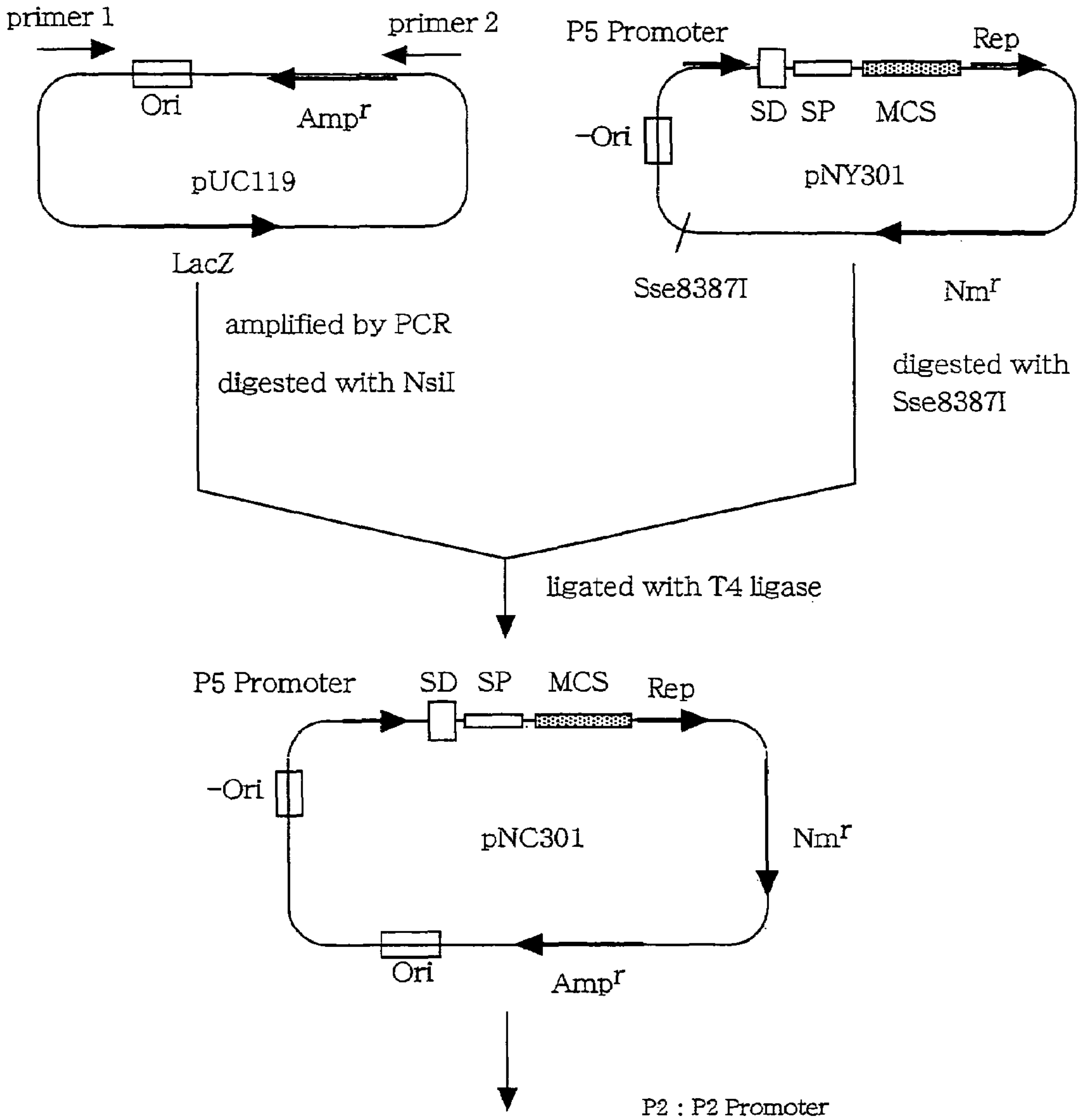
FIG. 22 shows a process of construction of plasmid shuttle vector pNCMO2.

Plasmid shuttle vector pNC301contains the P5 promoter from the HWP promoter region of *Brevibacillus choshinensis* HPD31, the neomycin resistance gene as a selective marker gene for the genus *Brevibacillus*, the ColE1 ori region as an origin of replication of *Escherichia coli* and the ampicillin resistance gene as a selective marker gene for *Escherichia coli*. It contains further the natural type HWP signal sequence as a secretion signal sequence (FIG. 22).

Figure 23:
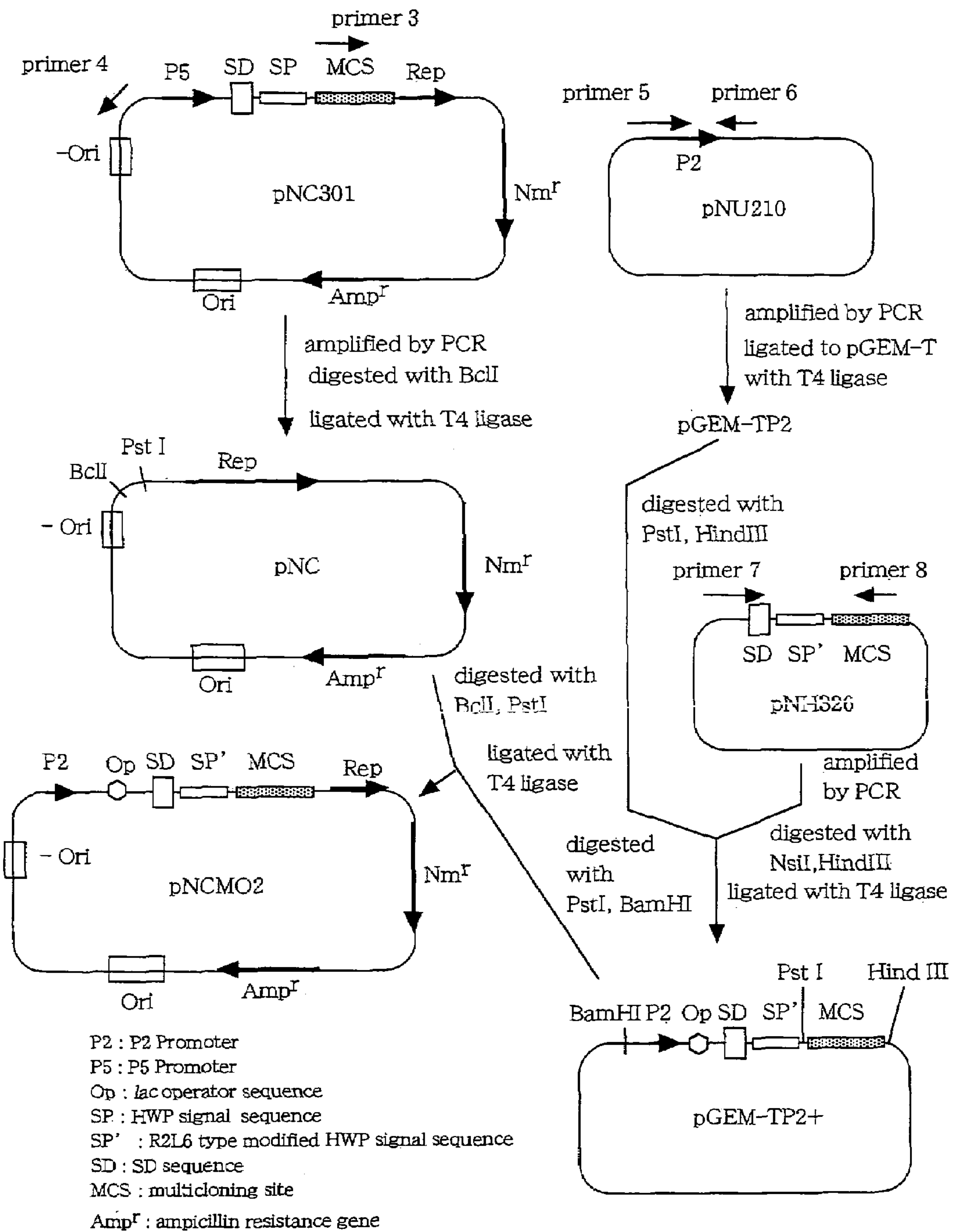
FIG. 23 shows a continuation of FIG. 22.

Construction of plasmid shuttle vector pNCMO2 is described below by referring to FIG. 23.

(2) Construction of Plasmid pNC

The total length of pNC301 obtained by excluding from plasmid shuttle vector pNC301 the HWP promoter region from *Brevibacillus choshinensis* HPD31 was amplified by PCR under condition 1 using primer 3 (Sequence No. 8: FIG. 8) and primer 4 (Sequence No. 9: FIG. 9). The amplified fragment of approximately 5 kbp was treated with BclI, and subjected to self-ligation with a T4 DNA ligase. *E. coli* JM109 was transformed with this DNA by the $CaCl_2$ method to obtain plasmid pNC. The reaction condition of PCR was (a cycle of a denaturation temperature: 94° C.-60 sec, an annealing temperature: 54° C.-120 sec and a DNA chain elongation temperature: 70° C.-180 sec was repeated 25 times).

(3) Construction of Plasmid pGEM-TP2

A DNA sequence encoding a P2 promoter from an HWP promoter region contained in plasmid pNU210 (Udaka, S. et al., Methods In Enzymology, 217, 23-33 (1993)) was amplified by PCR under condition 1 using primer 5 (Sequence No. 10: FIG. 10) and primer 6 (Sequence No. 11: FIG. 11) to obtain a DNA fragment of approximately 140 bp. Since primer 6 contains a lac operator sequence, this DNA fragment contains the lac operator sequence at the 3'-terminus of the P2 promoter. This fragment was ligated to pGEM-T (made by Promega) with a T4 DNA ligase. *E. coli* JM109 was transformed with this DNA by the $CaCl_2$ method, and a plasmid was extracted from the resulting ampicillin resistance transformant to obtain pGEM-TP2.

(4) Construction of Plasmid pGEM-TP2$^+$

A DNA sequence contained in plasmid pNH326 (Kajino, T., et al., Appl. Environ, Microbiol., 66, 638-642 (2000)), which contains SD1 and SD2 sequences of an HWP promoter region of *Brevibacillus choshinensis* HPD31, an R2L6 type modified HWP signal sequence (JP-A 7-170984 (1995))(Sequence No. 5, Sequence No. 21: FIG. 5) as a secretion signal sequence and a multicloning site, was amplified by PCR under condition 1 using primer 7 (Sequence No. 12: FIG. 12) and primer 8 (Sequence No. 13: FIG. 13) to obtain a DNA fragment of approximately 270 bp. The resulting DNA fragment was treated with restriction endonucleases NsiI and HindIII, and ligated to a PstI/HindIII site of pGEM-TP2 with a T4DNA ligase. *E. coli* JM109 was transformed with this DNA by the competent cell method to obtain pGEM-TP2+.

(5) Construction of Plasmid Shuttle Vector pNCMO2

Further, pGEM-TP2 +was treated with BamHI and PstI. The resulting fragment of approximately 400 bp was inserted into a BclI/PstI site of pNC, ligated with a T4 DNA ligase, and *E. coli* JM109 was transformed with this DNA by the CaCl2 method. A plasmid was extracted from the resulting ampicillin resistant transformant to obtain novel plasmid shuttle vector pNCMO2 (FIG. 23). The construction outline of plasmid shuttle vector pNCMO2 is shown in FIGS. 22 and 23. The restriction map of the thus-obtained novel plasmid shuttle vector pNCMO2 and the nucleotide sequence of its part containing a promoter and the like were shown in FIG. 21. In the above-mentioned manner, *Brevibacillus choshinensis* HPD31-S5 (FERM BP-6623) was transformed using this plasmid shuttle vector, and the resulting transformant (*Brevibacillus choshinensis* HPD31-S5/pNCMO2) was internationally deposited as FERM BP-7394.

Example 2

Transformation Efficiency of pNCMO2 and pNC301

A transformation efficiency of pNCMO2 and pNC301 is shown in Table 1. The transformation efficiency of both vectors to *E. coli* JM109 was satisfactorily high. The transformation efficiency of pNCMO2 to *Brevibacillus choshinensis* HPD31-S5 was low, as compared with that of pNC301, but high enough to insert the constructed plasmid. The transformation of *E. coli* JM109 was performed by the $CaCl_2$ method (Molecular Cloning, Cold Spring Harbor Laboratory, Press, 1, 82, (1989)), and the transformation of *Brevibacillus choshinensis* HPD31-S5 was performed by electroporation (Takagi, H. et al., Agric. Biol. Chem., 53, 3099-3100 (1989)). The electroporation was performed under conditions of 1.5 kV, 1000 Ω, 25 μF and 1.8 msec using Gene Pulser (manufactured by BioRad).

TABLE 1

Transformation efficiency of pNCMO2 and pNC301

| Plasmid vector | Host bacterium | Transformation efficiency (CFU/μgDNA) |
|---|---|---|
| pNOMO2 | *E. coli* JM109 | $6.1 \times 10^6$ |
| pNC301 | *E. coli* JM109 | $8.6 \times 10^6$ |
| pUC119 | *E. coli* JM109 | $1.9 \times 10^7$ |
| pNCMO2 | *Brevibacillus choshinensis* HPD31-S5 | $5.2 \times 10^4$ |
| pNC301 | *Brevibacillus choshinensis* HPD31-S5 | $1.2 \times 10^6$ |
| pNY301 | *Brevibacillus choshinensis* HPD31-S5 | $1.9 \times 10^6$ |

Example 3

Comparison of BLA Production Between Plasmid Shuttle Vector pNCMO2 and Plasmid Shuttle Vector pNC301

Figure 24:
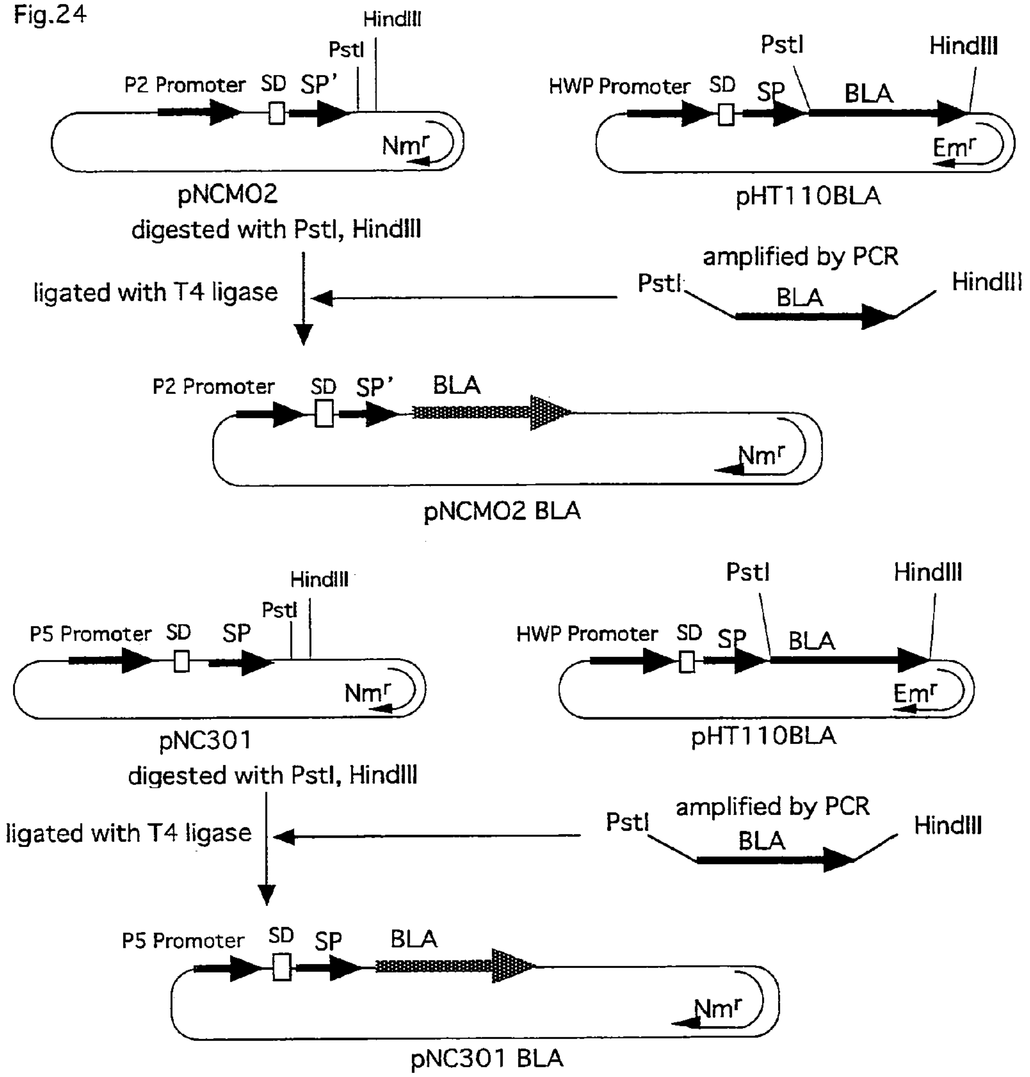
FIG. 24 shows a process of construction of recombinant gene expression plasmids pNCMO2BLA and pNC301BLA.

(1) Construction of Recombinant Gene Expression Plasmids pNCMO2BLA and pNC301BLA An α-amylase (BLA) gene from *Bacillus licheniformis* was amplified by PCR with pHY4631 (Yamagata, H. et al., J. of Biotechnol, 169, 1239-1245 (1987)) as a template using primer 9 (Sequence No. 14: FIG. 14) and primer 10 (Sequence No. 15: FIG. 15). The resulting PCR product was digested with restriction endonucleases PstI and HindIII to obtain a BLA gene-containing DNA fragment of approximately 1.5 kb. Plasmid vectors pNCMO2 and pNC301 constructed in Example 1 were digested with restriction endonucleases PstI and HindIII, and the above-obtained BLA gene-containing fragment was ligated thereto with a T4DNA ligase to obtain plasmid vectors pNCMO2BLA and pNC301BLA (FIG. 24). Further, *E. coli* JM109 was transformed by the $CaCl_2$ method using plasmid vectors pNCMO2BLA and pNC301BLA to obtain transformants *E. coli* JM109/pNCMO2BLA and *E. coli* JM109/pNC301BLA carrying plasmid vectors pNCMO2BLA and pNC301BLA respectively.

Further, as a BLA gene, it was also possible to use a DNA fragment cleaved from a BLA gene-containing plasmid, for example, pHT110BLA (Japanese Patent No. 2727391).

(2) BLA Production with *E. coli* JM109/pNCMO2BLA and *E. coli* JM109/pNC301BLA

Figure 25:
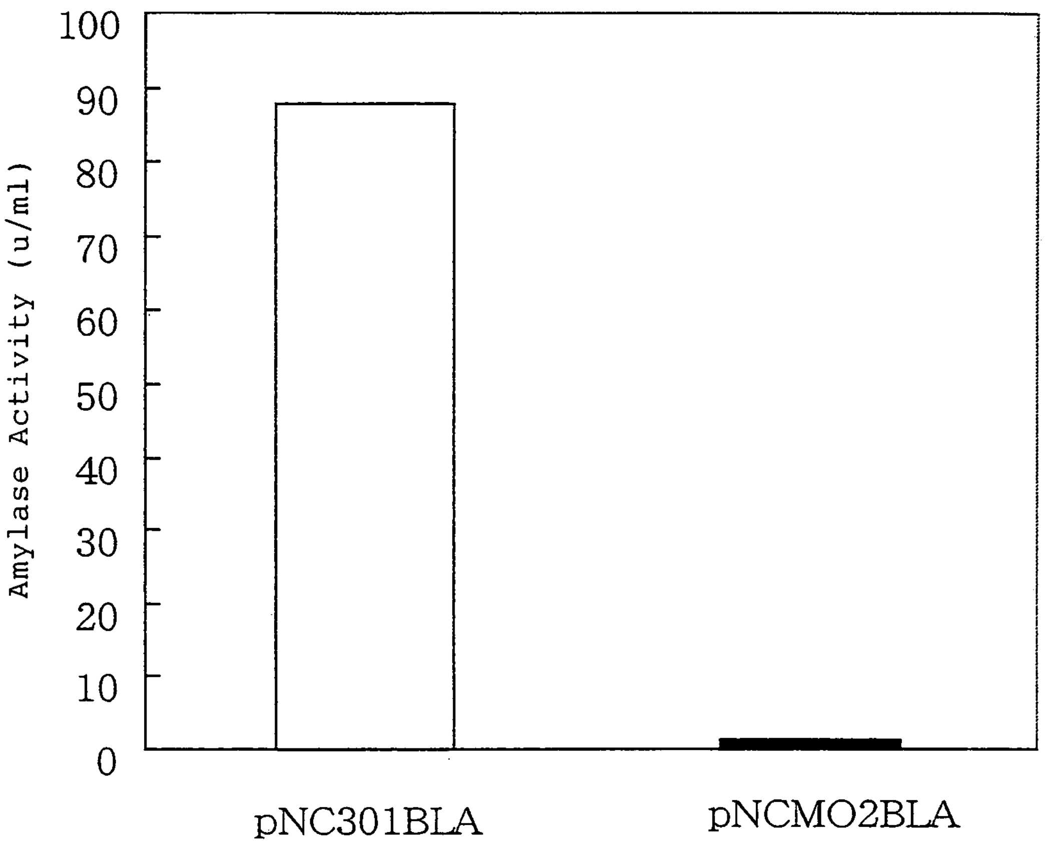
FIG. 25 shows a productivity of *E. coli* JM109/pNCMO2BLA and *E. coli* JM109/pNC301BLA.

Each of the transformants was inoculated to 1.5 ml portion of 2×YT medium, an incubated overnight at 37° C. with shaking. This culture solution was treated with a sonicator for 30 seconds to disrupt the cells, and the amylase activity in the treated solution was measured by the Saito's-method (Arch. Biochem. Biophys., 155, 290 (1973)) using a soluble starch as a substrate (FIG. 25). *E. coli* JM109/pNCMO2BLA produced amylase in an amount which was approximately 1/70 in comparison to *E. coli* JM109/pNC301BLA, and the gene expression in *Escherichia coli* was efficiently suppressed.

Figure 26:
FIG. 26 is a photo in place of a drawing, showing a halo formability and growth by *E. coli* JM109/pNCMO2BLA and *E. coli* MP109/pNC301BLA.

Further, *E. coli* JM109/pNCMO2BLA and *E. coli* JM109/pNC301BLA were inoculated on an LA agar medium containing 3% starch, and incubated overnight at 37+ C. to form colonies, and a halo formability and growth thereof were compared (FIG. 26: photo in place of a drawing). As a result, *E. coli* JM109/pNCMO2BLA was smaller in size of the halo around the colony than *E. coli* JM109/pNC301BLA, and the BLA expression was therefore suppressed. Moreover, from the size of the colony grown, it was found that *E. coli* JM109/pNCMO2BLA was proliferated faster. This is presumably because the BLA expression was suppressed at good efficiency in *E. coli* JM109/pNCMO2BLA and the stress exerted on the bacteria was therefore reduced to improve the amplification.

Figure 27:
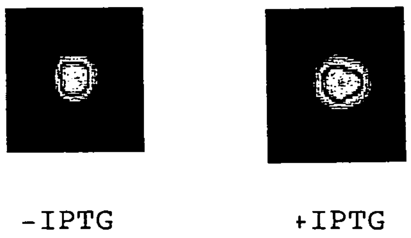
FIG. 27 is a photo in place of a drawing, showing effects of IPTG with respect to BLA expression by *E. coli* JM109/pNCMO2BLA.

When *E. coli* JM109/pNCMO2BLA was incubated on an agar medium containing 1 mM IPTG, the size of the halo formed was almost the same as that of the halo formed with the same strain incubated on a IPTG-free agar medium (FIG. 27: photo in place of a drawing). With respect to the expression suppressing effect in *Escherichia coli* provided by pNCMO2, this is presumably because in addition to the suppressing effect by inserting the lac operator, the P2 promoter activity is quite low in *Escherichia coli*, as compared with the P5 promoter activity.

(3) BLA Production with *Brevibacillus choshinensis* HPD31-S5/pNCMO2BLA and *Brevibacillus choshinensis* HPD31S5/pNC301BLA

Figure 28:
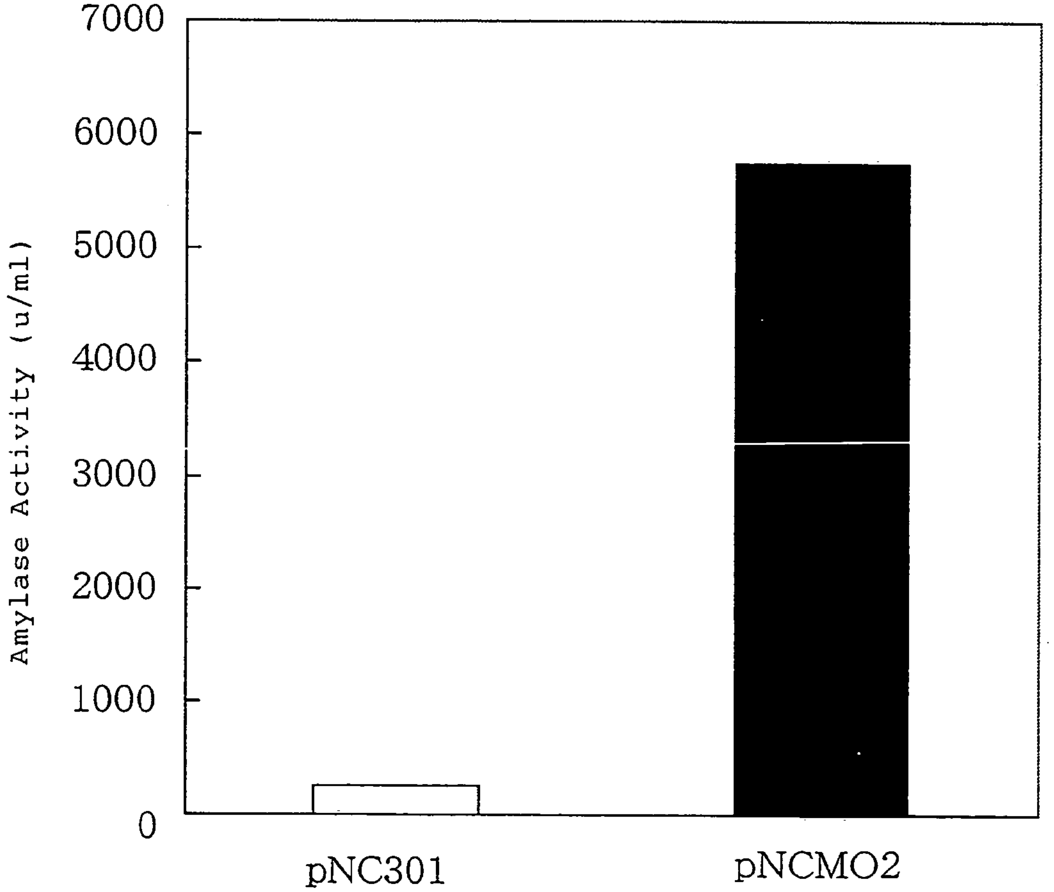
FIG. 28 shows a productivity of BLA by *Brevibacillus choshinensis* HPD31-S5/pNCMO2BLA and *Brevibacillus choshinensis* HPD31-S5/pNC301BLA.

*Brevibacillus choshinensis* HPD31-S5 was transformed by electroporation with plasmid vectors pNCMO2BLA and pNC301BLA obtained in (1) respectively to obtain transformants *Brevibacillus choshinensis* HPD31-S5/pNCMO2BLA and *Brevibacillus choshinensis* HPD31-S5/pNC301BLA carrying plasmid vectors pNCMO2BLA and pNC301BLA respectively (FIG. 24). The electroporation was performed under conditions of 1.5 kV, 1,000 Ω, 25 μF and 1.8 msec using Gene Pulser (manufactured by BioRad). Each of the transformants was inoculated in a test tube containing 1.5 ml TMN medium, and incubated at 30° C. for 2 days with shaking. This culture solution was centrifuged, and the amylase activity of the culture supernatant was measured by the Saito's method (Arch. Biochem. Biophys., 155, 290 (1973)) using a soluble starch as a substrate (FIG. 28). *Brevibacillus choshinensis* HPD31-S5/pNCMO2BLA produced amylase in an amount which was approximately 22 times as large as *Brevibacillus choshinensis* HPD31-S5/pNC301BLA. Consequently, it was shown that pNCMO2 can express a gene in bacteria of the genus *Brevibacillus* far more efficiently than pNC301.

Example 4

Construction of Recombinant Gene Expression Plasmid pNY326CT (1) Obtainment of CTA Gene and CTB Gene A cholera toxin (CT) A subunit gene (CTA)(0.7 bp) was amplified by PCR with a *Vibrio cholerae* chromosomal DNA (Mekalanos, J. et al., Nature, 306, 551-557 (1983)) as a template using two synthetic primers, primer 11 (Sequence No. 16: FIG. 16) and primer 12 (Sequence No. 17: FIG. 17). In like manner, a CT B subunit gene (CTB)(0.3 bp) was amplified using two primers, primer 13 (Sequence No. 18: FIG. 18) and primer 14 (Sequence No. 19: FIG. 19).

(2) Plasmid pT7BlueCTA and plasmid pT7BlueCTB

Plasmid pT7Blue (made by Novagen) and the above-obtained CTA gene or CTB gene were ligated with a T4 ligase to obtain plasmid pT7BlueCTA carrying the CTA gene or plasmid pT7BlueCTB carrying the CTB gene.

(3) Construction of Plasmid pNY326CTA

Plasmid pNY326 [plasmid obtained by converting the signal sequence of pNY301(JP-A 10-295378 (1998)) to an R2L6 type (Sequence Nos. 5, 21: FIG. 5)] was treated with NcoI and HindIII to obtain a fragment of 3.6 kbp. Further, pT7BlueCTA was treated with NcoI and HindIII to obtain a CTA gene-containing DNA fragment of 0.7 kbp. This DNA fragment was ligated to the above-obtained gene fragment of 3.6 kbp with a T4 DNA ligase. *Brevibacillus choshinensis* HPD31-S5 was transformed by electroporation using the ligated DNA. From the resulting neomycin resistant strain, a plasmid was extracted to obtain pNY326CTA carrying the CTA gene.

(4) Construction of Plasmid pNY326CTB

In like manner, pNY326 was treated with NcoI and BamHI to obtain a DNA fragment of 3.6 kbp. Further, pT7BlueCTB was treated with NcoI and BamHI to obtain a CTB gene-containing DNA fragment of 0.3 kbp. This DNA fragment was ligated to the above-obtained DNA fragment of 3.6 kbp with a T4 DNA ligase. *Brevibacillus choshinensis* HPD31-S5 was transformed using the ligated DNA to select a strain having a neomycin resistance. From the selected strain, a plasmid was extracted to obtain plasmid pNY326 CTB carrying the CTB gene.

(5) Trial of Transformation of *Brevibacillus choshinensis* HPD31-S5 with pNY326CT pNY326CTB was treated with BamHI and HindIII to obtain a DNA fragment of 4.7 kbp. Further, a CTA gene in the form containing a SD2 sequence (SD-CTA gene (0.8 kbp)) was amplified by PCR with pNY326CTA as a template using two primers, primer 15 (Sequence No. 20: FIG. 20) and primer 11 (Sequence No. 16: FIG. 16). The PCR product was treated with BamHI and HindIII to obtain a fragment of 0.4 kbp. This fragment was ligated to the above-obtained DNA fragment of 4.7 kbp from pNY326CTB with a T4 DNA ligase. *Brevibacillus choshinensis* HPD31-S5 was transformed by electroporation using the ligated DNA, and the transformant was spread on a 50 μg/ml neomycin-containing TM agar medium (1% peptone, 0.2% yeast extract, 0.5% meat extract, 1% glucose, 0.001% $FeSO_4.7H_2O$, 0.001% $MnSO_4.4H_2O$, 0.0001% $ZnSO_4.7H_2O$, 1.5% agar, pH 7.0) to try to select a strain having a neomycin resistance. However, the resistant strain was not obtained. The electroporation was performed under conditions of 1.5 kV, 1,000 Ω, 25 μF and 1.8 msec using Gene Pulser (manufactured by BioRad).

Example 5

Figure 29:
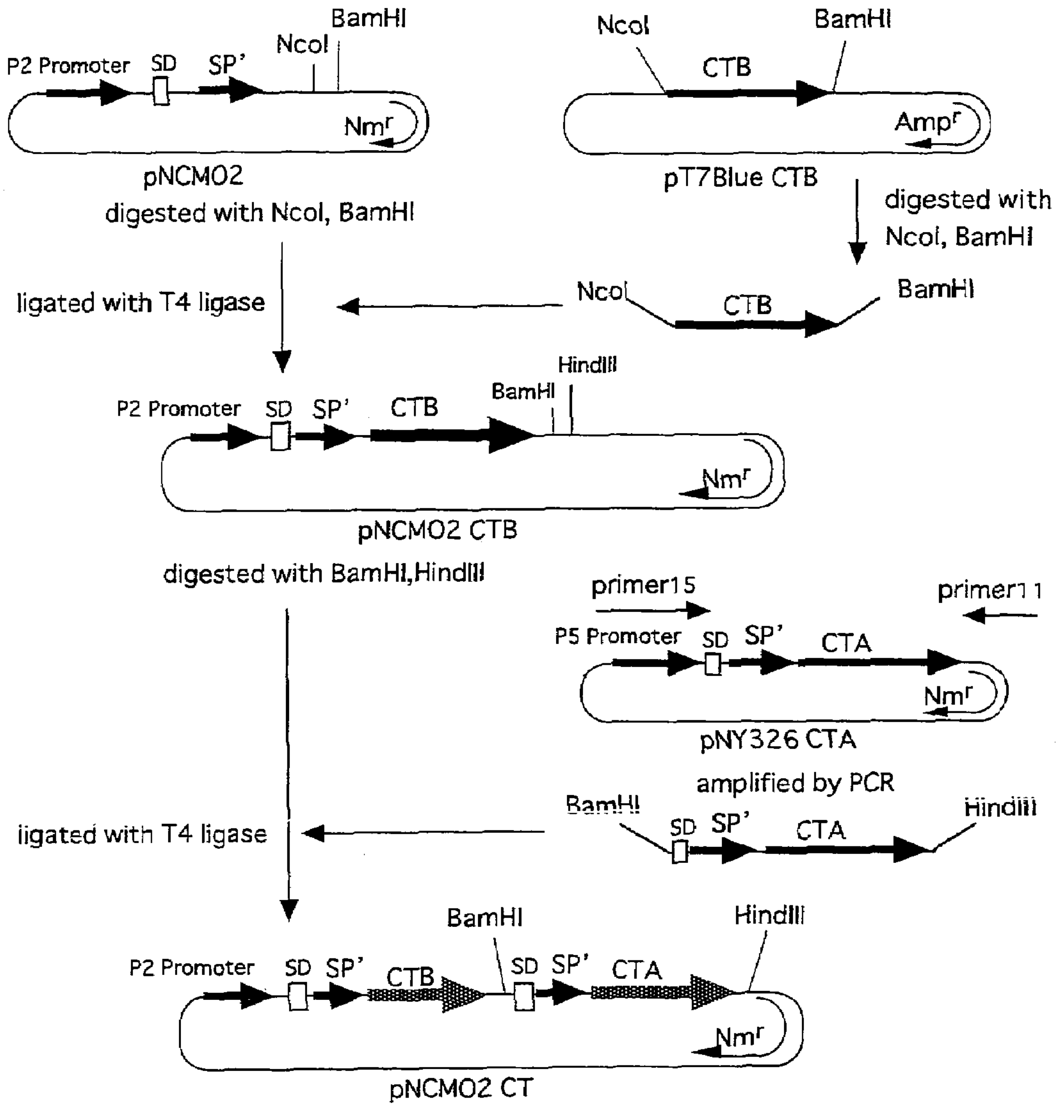
FIG. 29 shows a process of construction of recombinant gene expression plasmid pNCMO2CT.

Construction of Recombinant Gene Expression Plasmid pNCMO2CT (1) Construction of Plasmid pNCMO2CTB pNCMO2 was treated with NcoI and BamHI to obtain a fragment of 5.2 kbp. Further, pT7BlueCTB was treated with NcoI and BamHI to obtain a CTB gene-containing DNA fragment of 0.3 kbp. This DNA fragment was ligated to the above-obtained gene fragment of 5.2 kbp with a T4 DNA ligase (FIG. 29). *E. coli* JM109 was transformed with this ligated DNA, and a plasmid was extracted to obtain pNCMO2CTB carrying the CTB gene.

(2) Construction of Plasmid pNCMO2CT pNCMO2 CTB was treated with BamHI and HindIII to obtain a fragment of 5.5 kbp. The SD-CTA gene (0.8 kbp) obtained in Example 4 (5) was treated with BamHI and HindIII to recover a fragment of 0.8 kbp. This fragment was ligated to the above-obtained gene fragment of 5.5 kbp with a T4 DNA ligase (FIG. 29). *E. coli* JM109 was transformed with the ligated DNA to select a transformant having an ampicillin resistance. From the three selected transformants, a plasmid was extracted to obtain plasmid pNCMO2CT carrying the CTB gene. As a result of sequencing, it was found that in all of the transformants, the CTB gene was correctly ligated to the plasmid. The transformants obtained here were designated *E. coli* JM109/pNCMO2CT. *Brevibacillus choshinensis* HPD31-S5 was transformed with pNCMO2CT extracted from *E. coli* JM109/pNCMO2CT by electroporation. Consequently, a large number of transformants carrying the same plasmid were obtained. The resulting transformants were designated *Brevibacillus choshinensis* HPD31-S5/pNCMO2CT. The electroporation was performed under conditions of 1.5 kV, 1,000 Ω, 25 μF and 1.8 msec using Gene Pulser (manufactured by BioRad).

(3) Expression of CT with *Brevibacillus choshinensis* HPD31-S5/pNCMO2CT

Figure 30:
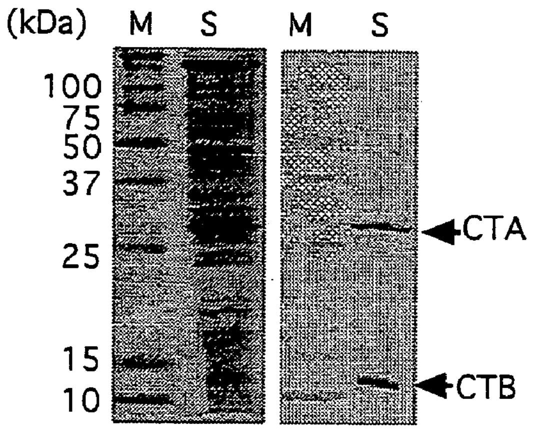
FIG. 30 is photos in place of a drawing, showing a Coomassie Brilliant Blue stain image and a western blotting image of a culture of transformant *Brevibacillus choshinensis* HPD31-S5/pNCMO2CT.

*Brevibacillus choshinensis* HPD31-S5/pNCMO2CT was cultured in 3 ml of a 50 μg/ml neomycin-containing TM liquid medium at 30° C. for 2 days using a medium-sized test tube while being shaken, and the culture supernatant was subjected to SDS-PAGE. The analysis was conducted by Coomassie Brilliant Blue staining and western blotting with a rabbit CT polyclonal antibody. The estimated molecular weights of CTA and CTB were 28 kDa and 12 kDa respectively, and showed staining bands in positions of corresponding molecular weights respectively. From the color depths of the bands, the secretory production amount of CTA was estimated at 70 mg/l and the secretory production amount of CTB at 30 mg/l respectively. Its SDS-PAGE electrophoresis pattern is shown in a photo in place of a drawing (FIG. 30). Further, when the culture supernatant was purified using a galactose resin specifically binding CT (Microbial Pathogenesis, 16, 71-79 (1994)) and the purified fraction was then subjected to electrophoresis without being heat-treated, the band was shifted to a site of approximately 90 kDa. From this fact, it was presumed that the expressed subunit took a 1A5B structure.

Effects of the Invention

According to the invention, the plasmid shuttle vector between *Escherichia coli* and bacteria of the genus *Brevibacillus* is provided. Further, the plasmid shuttle vector of the invention, as shown in the results of the expression of the BLA gene in Example 3, suppresses the gene expression in *Escherichia coli* and can allow the efficient gene expression in *Brevibacillus choshinensis*. As shown by the expression of CT in Examples 4 and 5, plasmid shuttle vector pNCMO2 in the invention is useful especially for construction of the recombinant gene expression plasmid requiring complex gene construction and for protein production with the transformant transformed with the said recombinant gene expression plasmid.

Description on Microorganisms Deposited Under Rule 13-2

1. *Brevibacillus choshinensis* HPD31-S5/pNCMO2 a. Name and address of a depositary agency in which this microorganism was deposited Name: International Patent Organism Depositary, National Institute of Advanced Industrial Science and Technology Address: AIST Tsukuba Central 6, 1-1-1 Higashi, Tsukuba Ibaraki, 305-8566, Japan b. Date on which the microorganism was deposited in the depositary agency of a Dec. 12, 2000 c. Receipt Number that the depositary agency of a assigned on the deposition FERM BP-7394

2. *Brevibacillus choshinensis* HPD31 (FERM BP-1087)

a. Name and address of a depositary agency in which this microorganism was deposited Name: International Patent Organism Depositary, National Institute of Advanced Industrial Science and Technology Address: AIST Tsukuba Central 6, 1-1-1 Higashi, Tsukuba Ibaraki, 305-8566, Japan b. Date on which the microorganism was deposited in the depositary agency of a Aug. 31, 1999 c. Receipt Number that the depositary agency of a assigned on the deposition FERM BP-6863

The invention claimed is:

1. A plasmid shuttle vector replicable in both *Brevibacillus choshinensis* and *Escherichia coli*, wherein said plasmid shuttle vector comprises the following DNA sequences:

(1) an origin sequence of replication functionable in *Escherichia coli*;

(2) an origin sequence of replication functionable in *Brevibacillus choshinensis;*

(3) a P2 promoter sequence;

(4) a lac operator sequence;

(5) an SD1 sequence;

(6) an SD2 sequence;

(7) a secretion signal sequence;

(8) a multicloning site sequence;

(9) an HS gene sequence;

(10) a Rep protein gene; and

(11) one member selected from the group consisting of the following members (a) and (b):

(a) a drug resistance gene functionable as a selective marker in *Brevibacillus choshinensis*, and a drug resistance gene functionable as a selective marker in *Escherichia coli*; and (b) a zeocin resistance gene, wherein a region comprising the DNA sequences (3)-(9) has a DNA sequence according to SEQ ID NO: 22.

2. The plasmid shuttle vector according to claim 1, wherein the drug resistance gene functionable as a selective marker in *Brevibacillus choshinensis* in member (a) of DNA sequence (11) is one member selected from the group consisting of a neomycin resistance gene and an erythromycin resistance gene, and the drug resistance gene functionable as a selective marker in *Escherichia coli* in member (a) of DNA sequence (11) is one member selected from the group consisting of a kanamycin resistance gene, an ampicillin resistance gene, and a chloramphenicol resistance gene.

3. A plasmid shuffle vector pNCMO2 comprising SEQ ID NO: 22 having the following restriction endonuclease recognition sequence sites:

4. A DNA sequence according to SEQ ID NO: 22.

5. A transformant obtained by transforming *Brevibacillus choshinensis* with a recombinant plasmid obtained by inserting a DNA sequence encoding a protein into the plasmid shuttle vector according to claim 1.

6. A transformant obtained by transforming *Brevibacillus choshinensis* with a recombinant plasmid obtained by insert-

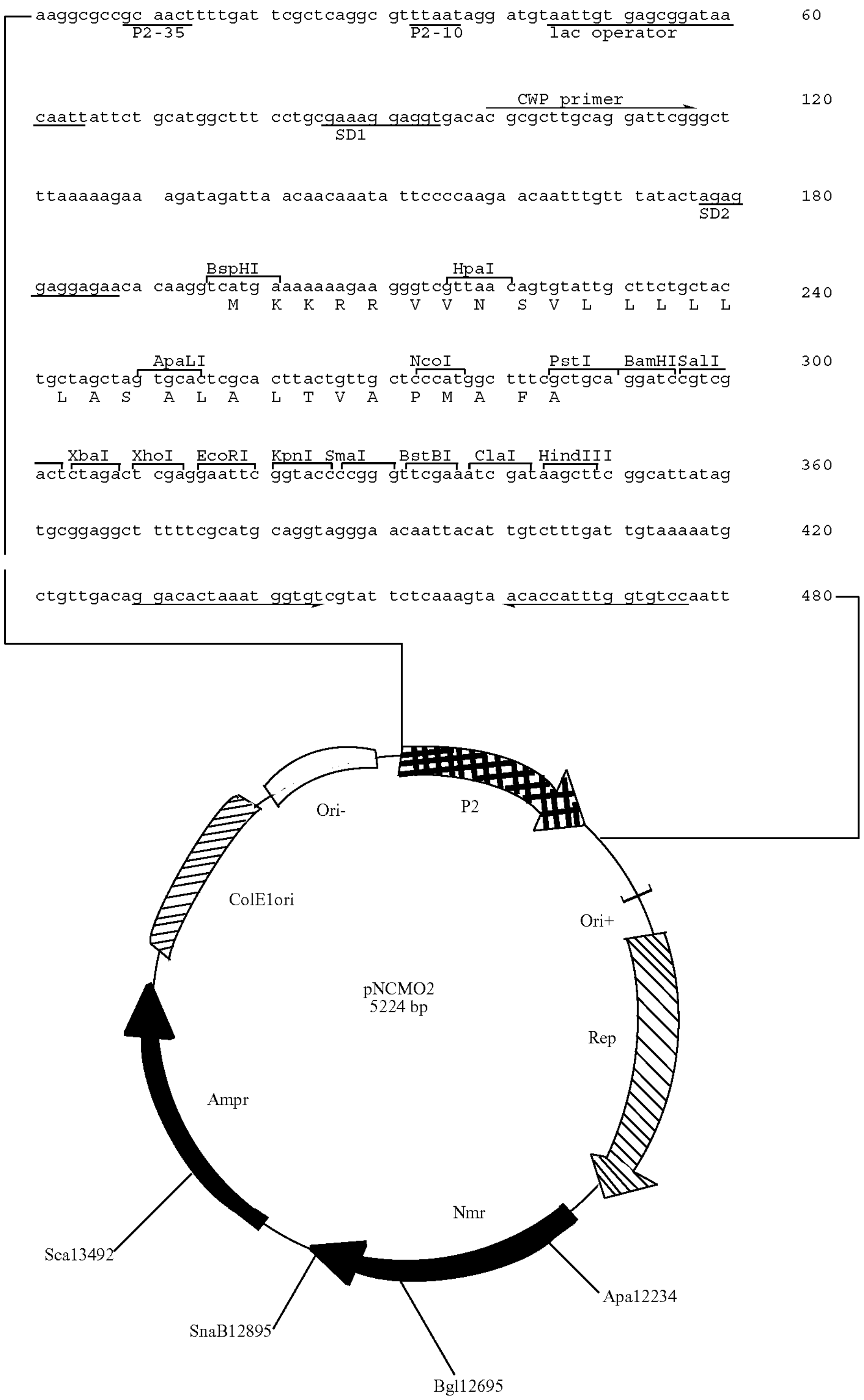

ing a DNA sequence encoding a protein into the plasmid shuttle vector according to claim 2.

7. A transformant obtained by transforming *Brevibacillus choshinensis* with a recombinant plasmid obtained by inserting a DNA sequence encoding a protein into the plasmid shuttle vector pNCMO2 according to claim 3.

8. A process for producing a protein, wherein said process comprises:

culturing the transformant according to claim 5 in a medium; and collecting the protein secreted and accumulated in the medium.

* * * * *

```
                          SEQUENCE LISTING

<160> NUMBER OF SEQ ID NOS: 21

<210> SEQ ID NO 1
<211> LENGTH: 44
<212> TYPE: DNA
<213> ORGANISM: Brevibacillus choshinensis

<400> SEQUENCE: 1

aaggcgccgc aacttttgat tcgctcaggc gtttaatagg atgt                        44


<210> SEQ ID NO 2
<211> LENGTH: 21
<212> TYPE: DNA
<213> ORGANISM: Escherichia coli

<400> SEQUENCE: 2

aattgtgagc ggataacaat t                                                 21


<210> SEQ ID NO 3
<211> LENGTH: 10
<212> TYPE: DNA
<213> ORGANISM: Brevibacillus choshinensis

<400> SEQUENCE: 3

gaaaggaggt                                                              10


<210> SEQ ID NO 4
<211> LENGTH: 12
<212> TYPE: DNA
<213> ORGANISM: Brevibacillus choshinensis

<400> SEQUENCE: 4

agaggaggag aa                                                           12
```

-continued

<210> SEQ ID NO 5
<211> LENGTH: 30
<212> TYPE: PRT
<213> ORGANISM: ARTIFICIAL SEQUENCE
<220> FEATURE:
<223> OTHER INFORMATION: SYNTHETIC DNA

<400> SEQUENCE: 5

```
Met Lys Lys Arg Arg Val Val Asn Ser Val Leu Leu Leu Leu Leu Leu
1               5                   10                  15

Ala Ser Ala Leu Ala Leu Thr Val Ala Pro Met Ala Phe Ala
            20                  25                  30
```

<210> SEQ ID NO 6
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
aaaatgcatg gccagcaaaa gg 22

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
aaaatgcatg acgaaagggc 20

<210> SEQ ID NO 8
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 8
aaatgatcaa agcttcggca ttatagtgcg gg 32

<210> SEQ ID NO 9
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
aaatgatcct gcaggatccg tcgactctag 30

<210> SEQ ID NO 10
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 10
aaaggatccg acataatgga cagg 24

-continued

<210> SEQ ID NO 11
<211> LENGTH: 52
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
aaactgcaga ataattgtta tccgctcaca attacatcct attaaacgcc tg 52

<210> SEQ ID NO 12
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
aaactgcatg gctttcctgc gaaagg 26

<210> SEQ ID NO 13
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
aaaagcttat cgatttcgaa ggg 23

<210> SEQ ID NO 14
<211> LENGTH: 23
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
cgctgcagca gcggcggcaa atc 23

<210> SEQ ID NO 15
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
aaaagcttat ctttgaacat aaattg 26

<210> SEQ ID NO 16
<211> LENGTH: 34
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
aaccatggct ttcgctacag atgataagtt atat 34

<210> SEQ ID NO 17
<211> LENGTH: 28
<212> TYPE: DNA
<213> ORGANISM: ARTIFICIAL SEQUENCE
<220> FEATURE:
<223> OTHER INFORMATION: SYNTHETIC DNA

-continued

```
<400> SEQUENCE: 17

ttaagcttca taattcatcc ttaattct                                  28


<210> SEQ ID NO 18
<211> LENGTH: 58
<212> TYPE: DNA
<213> ORGANISM: ARTIFICIAL SEQUENCE
<220> FEATURE:
<223> OTHER INFORMATION: SYNTHETIC DNA

<400> SEQUENCE: 18

aaccatggct ttcgctacac ctcaaaatat tactgatttg tgtgcagaat accacaac  58


<210> SEQ ID NO 19
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 19

aaggatcctt aatttgccat actaattgcg gc                              32


<210> SEQ ID NO 20
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 20

gcggatccag aggaggagaa cacaaggtc                                  29


<210> SEQ ID NO 21
<211> LENGTH: 90
<212> TYPE: DNA
<213> ORGANISM: ARTIFICIAL SEQUENCE
<220> FEATURE:
<223> OTHER INFORMATION: SYNTHETIC DNA

<400> SEQUENCE: 21

atgaaaaaaa gaagggtcgt taacagtgta ttgcttctgc tactgctagc tagtgcactc  60

gcacttactg ttgctcccat ggctttcgct                                  90
```